United States Patent [19]

Vidgrén et al.

[11] Patent Number: 5,724,962
[45] Date of Patent: Mar. 10, 1998

[54] VALVE FOR USE IN CONNECTION WITH AN INHALER APPARATUS

[75] Inventors: Mika Tapio Vidgrén, Kuopio; Tapio Antti Kaplas, Kerava, both of Finland

[73] Assignee: Orion-Yhtymä Oy, Espoo, Finland

[21] Appl. No.: 416,732

[22] PCT Filed: Oct. 14, 1993

[86] PCT No.: PCT/FI93/00421

§ 371 Date: Apr. 12, 1995

§ 102(e) Date: Apr. 12, 1995

[87] PCT Pub. No.: WO94/08651

PCT Pub. Date: Apr. 28, 1994

[30] Foreign Application Priority Data

Oct. 15, 1992 [FI] Finland ............... 924661

[51] Int. Cl.⁶ .................................... A61M 16/00
[52] U.S. Cl. ................. 128/205.24; 128/204.18; 128/200.23; 128/200.14; 128/201.28
[58] Field of Search ........... 128/200.23, 200.14, 128/200.24, 201.28, 203.11, 203.12, 203.18, 203.28, 205.24, 206.15, 207.1, 207.16, 204.18

[56] References Cited

U.S. PATENT DOCUMENTS

| | | |
|---|---|---|
| 3,630,197 | 12/1971 | Hirano . |
| 4,470,412 | 9/1984 | Nowacki et al. ............ 128/200.23 |
| 4,534,343 | 8/1985 | Nowacki et al. . |
| 4,622,964 | 11/1986 | Flynn . |
| 4,854,561 | 8/1989 | Sperry . |
| 5,042,467 | 8/1991 | Foley ........................... 128/200.14 |
| 5,103,854 | 4/1992 | Bailey et al. . |
| 5,385,140 | 1/1995 | Smith ........................... 128/200.23 |

FOREIGN PATENT DOCUMENTS

| | | |
|---|---|---|
| 0 139 363 | 5/1985 | European Pat. Off. . |
| WO 92/06728 | 4/1992 | WIPO . |

OTHER PUBLICATIONS

"Valves for Use in Controlled Ventilation The Takaoka Inflating Valve", *Automatic Ventilation of the Lungs*, William W. Mushin et al., 1980, Blackwell Scientific Publications, Oxford, Great Britain, p. 847.

"Valves for Use in Controlled Ventilation The Newton Inflating Valve", *Automatic Ventilation of the Lungs*, William W. Mushin et al., 1980, Blackwell Scientific Publications, Oxford, Great Britain, p. 841.

*Primary Examiner*—Vincent Millin
*Assistant Examiner*—William J. Deane, Jr.
*Attorney, Agent, or Firm*—Burns, Doane, Swecker & Mathis, L.L.P.

[57] ABSTRACT

A valve for use in connection with aerosol spacers to be mounted on a metered dose inhaler, characterized in that the valve comprises a frame portion (1) one end of which can be attached to the chamber portion of known aerosol spacers and its other end constitutes a mouthpiece having an air outlet aperture (4) for expiratory air and an air inlet aperture (6) for the air to be inhaled via the inhaler chamber, and a flap (3) which is to be fitted inside the mouthpiece and slides freely in the direction of the longitudinal axis of the mouthpiece so that, upon inhalation, it will open the air inlet aperture (6) and close the air outlet aperture (4) and upon exhalation, it will close the air outlet aperture (4), and upon exhalation, it will open the air outlet aperture (4) and close the air inlet aperture (6).

13 Claims, 1 Drawing Sheet

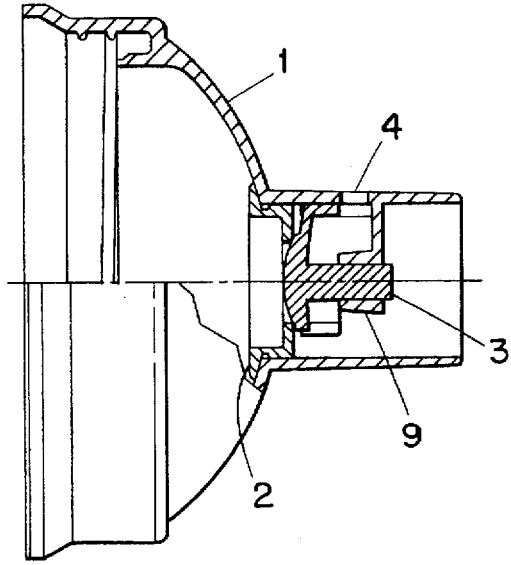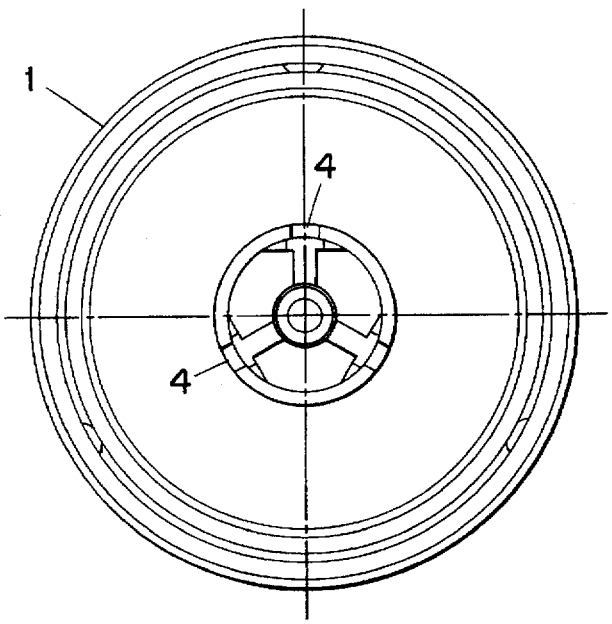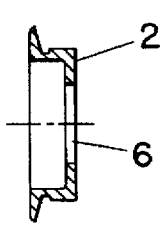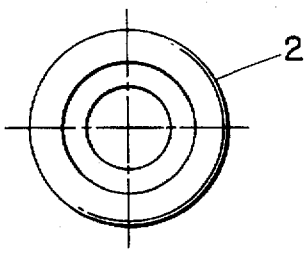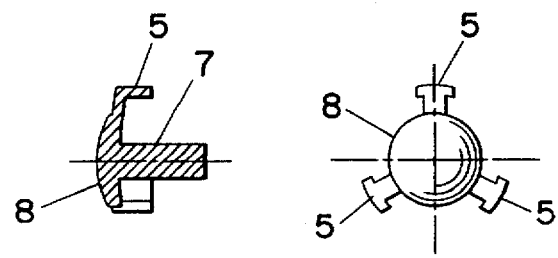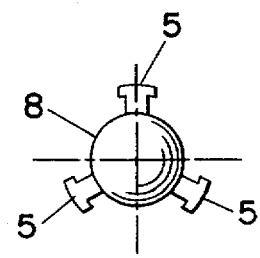

VALVE FOR USE IN CONNECTION WITH AN INHALER APPARATUS

FIELD OF THE INVENTION

The invention relates to an improved valve and mouthpiece for use in auxiliary inhalation devices to be mounted on pressurized metered dose inhalers.

BACKGROUND OF THE INVENTION

A pressurized metered dose inhaler is the most commonly used means of administering medicaments by inhalation. However, the use of a metered dose inhaler involves problems owing to which only a relatively small proportion (10–25%) of the medicament dose released from the metered dose inhaler will pass into the lungs. The technique of using a metered dose inhaler is of great importance for the success of medicament therapy. The patient should trigger the aerosol at the initial stage of a calm and long inhalation. Learning this is, however, difficult for a very large proportion of asthma patients. Furthermore, the aerosol spray released at a high velocity from a metered dose inhaler will impinge against the patient's throat, causing adverse local and systemic side effects.

A number of aerosol holding containers, or so-called aerosol spacers, have been developed to facilitate the use of a metered dose inhaler and to improve the passage of the medicament to the lungs. When an aerosol spacer is used, the aerosol dose can first be released from the metered dose inhaler into a chamber from which the patient can inhale it into his lungs at his own inhalation pace. However, in order for this to be possible, the mouthpiece of the spacer must be equipped with a valve which will open automatically upon inhalation via the mouthpiece of the spacer and will close automatically during exhalation via the mouthpiece. Thus a patient can inhale a dose of medicament in his inhalation via the valve. Furthermore, the valve makes normal exhaling possible before and after inhalation.

Such an aerosol spacer, equipped with an aerosol chamber and one or two valves, has been disclosed in, for example, Finnish patent application No. 792802. FIGS. 4 and 5 of the said patent application show a one-valve system. In it the patient first releases a dose of medicament from the metered dose inhaler into the spacer. The patient's inhalation will automatically open the valve between the chamber and the mouthpiece, enabling the medicament to be inhaled along with the inspiratory air flowing through the chamber. Upon exhalation the valve will close. The mouthpiece of the aerosol spacer is equipped with apertures through which expiratory air will be discharged, the valve preventing exhalation into the chamber. Such a system has a disadvantage in that during inhalation a considerable proportion of the inspiratory air is inhaled through the apertures of the mouthpiece. In this case, in order that the entire air volume contained in the aerosol spacer (most commonly 750 ml) could be emptied with one inhalation, the patient should be able to inhale an air volume considerably larger than this. This causes considerable difficulties for patients with severe asthma, and in particular for old people and children.

FIGS. 1–3 of the said patent application disclose a mouthpiece provided with two valves, eliminating the above disadvantage. The first valve permits the air to be inhaled to pass from the chamber into the mouthpiece and prevents expiratory air from returning to the chamber. The second valve permits an expiratory air flow through the aperture of the mouthpiece but prevents inhalation through this aperture. Such an aerosol spacer provided with two valves is, however, unnecessarily complicated and expensive.

SUMMARY OF THE INVENTION

The present invention relates to a valve for an aerosol spacer to be mounted on a metered dose inhaler; with the help of the valve, upon inhalation the entire volume of inspiratory air will pass through the chamber, and during exhalation the entire air volume will be directed via the apertures of the mouthpiece. The valve system according to the invention is considerably simpler than known systems. By the use of the system according to the invention, the two-valve structure according to patent application 792802 can be replaced with one valve.

BRIEF DESCRIPTION OF THE DRAWINGS FIGURES

The invention is described below in greater detail with reference to the specification of the invention and the accompanying drawings.

FIG. 1 is a cross sectional representation of one preferred embodiment of the valve according to the invention.

FIG. 2 is a cross sectional representation of one preferred embodiment of the flap of the valve according to the invention.

FIG. 3 is a cross sectional representation of one preferred embodiment of the flap seat of the valve according to the invention.

DETAILED DESCRIPTION OF THE INVENTION

FIG 1 depicts a valve according to the invention, having a hollow frame portion (1) open at both ends. One end of the frame portion (1) is capable of being coupled, for example by means of a threading, to the aerosol chamber portion of known aerosol inhalers, and its other end constitutes a cylindrical mouthpiece, so that a continuous air passageway is formed from the cheer to the mouthpiece. The wall of the mouthpiece has three air outlet apertures (4) for expiratory air. Inside the mouthpiece there is a cylindrical fitting (9) which is part of the frame portion, an air outlet flap (3), equipped with closing leaves (5), being mounted in the fitting. The fitting (9) adjoins the mouthpiece by one of more support legs.

The flap (3) shown in FIG. 2 is made up of a spindle-like projection (7) and a convex end portion (8) equipped with three leaves (5) for closing the air outlet aperture. The spindle-like projection of the flap (3) is mounted in the loose cylindrical fitting (9) in the frame portion, so that the flap (3) will slide in the fitting freely in a direction parallel to the mouthpiece. The flap seat (2) having the shape of the circular frame, shown in FIG. 3, is fastened to the chamber-side end of the mouthpiece, so that it will at the same time form an air inlet aperture (6) for air to be inhaled via the inhaler chamber. In this case the flap (3), sliding in the fitting, will in its one extreme position with its convex end portion close the air inlet aperture (6) and at the same time open the air outlet apertures (4) (exhalation), and will in its other extreme position with its closing leaves (5) close the air outlet apertures (4) and at the same time open the air inlet aperture (6) (inhalation).

When the patient inhales via the mouthpiece, the flap (3) will move in the fitting so that it will open the inlet aperture (6) and at the same time close the air outlet apertures (4), whereupon all the air to be inhaled will pass through the chamber. Upon exhalation the flap (3) will open the air outlet apertures (4) and at the same time close the air inlet aperture (6), whereupon expiratory air will be channeled out via the air outlet apertures of the mouthpiece. Thus the patient can breathe freely through the mouthpiece before and after the inhalation. The valve system according to the invention is simple and, when necessary, easy to dismantle and clean.

The structure shown in the drawings can be modified in a variety ways within the scope of the invention. For example, the number of air outlet apertures and the corresponding closing leaves may be one or more. Likewise, the frame portion can be attached to the chamber portion or mouthpiece of known aerosol spacers in many ways, for example by friction.

We claim:

1. A valve for use in connection with aerosol spacers to be mounted on a metered dose inhaler, comprising a frame portion having one end for attachment to a chamber portion of an aerosol spacer and an opposite end defining a mouthpiece that possesses a longitudinal axis, the mouthpiece being defined by a wall portion which possesses an inner surface, said mouthpiece having at least one air outlet aperture positioned in said wall portion for expiratory air and an air inlet aperture for air to be inhaled via the chamber portion of the aerosol spacer, and a flap fitted inside the mouthpiece, the flap comprising an end portion for closing the air inlet aperture during exhalation and a closing leaf for closing the at least one air outlet aperture during inhalation, the whole flap being slidably movable in a direction substantially parallel to the longitudinal axis of the mouthpiece to cause the closing leaf to slide along the inner surface of the wall portion so that upon inhalation the flap will slide to a position to open the air inlet aperture and close the at least one air outlet aperture, and so that upon exhalation the flap will slide to a position to open the at least one air outlet aperture and close the air inlet aperture.

2. A valve according to claim 1, wherein said frame portion includes a fitting, said flap being mounted in said fitting.

3. A valve according to claim 1, wherein said air inlet aperture is formed by a ring shaped flap seat.

4. A valve according to claim 1, wherein the flap includes an end portion which closes the air inlet aperture during exhalation, and a projection, said frame portion including a fitting in which is slidably fitted the projection of the flap.

5. A valve according to claim 1, wherein the mouthpiece includes a plurality of spaced apart air outlet apertures.

6. A valve according to claim 5, wherein said flap includes a plurality of closing leafs which each close one of the air outlet apertures during inhalation.

7. A valve for use in connection with aerosol spacers to be mounted on an inhaler, comprising a frame portion having one end for attachment to a chamber portion of an aerosol spacer and an opposite end defining a mouthpiece that possesses a longitudinal axis, the mouthpiece having an at least one air outlet aperture for expiratory air and an air inlet aperture for inhalation of air via the chamber portion of the aerosol spacer, and a flap fitted inside the mouthpiece and slidably movable in a direction substantially parallel to the longitudinal axis of the mouthpiece between a first position and a second position, the flap including a first portion for effecting opening and closing of the air inlet aperture and a second portion for effecting closing and opening of the at least one air outlet aperture, the first portion and the second portion of the flap being formed as one piece so that movement of the first portion results in movement of the second portion and so that movement of the first portion requires movement of the second portion, and so that upon inhalation both the first portion and the second portion of the flap slide to a position in which the first portion of the flap is positioned to open the air inlet aperture and the second portion of the flap is positioned to close the at least one air outlet aperture, and upon exhalation both the first portion and the second portion of the flap slide to a position in which the first portion of the flap is positioned to close the air inlet aperture and the second portion of the flap is positioned to open the air outlet aperture.

8. A valve according to claim 7, wherein said frame portion includes a fitting, said flap being mounted in said fitting.

9. A valve according to claim 7, wherein said air inlet aperture is formed by a ring shaped flap seat.

10. A valve according to claim 7, wherein the first portion of the flap includes an end portion and the second portion of the flap includes a closing leaf, the flap including a projection and said frame portion including a fitting in which is slidably fitted the projection of the flap.

11. A valve according to claim 7, wherein the mouthpiece includes a plurality of spaced apart air outlet apertures.

12. A valve according to claim 11, wherein said first portion includes a plurality of spaced apart closing leafs which each close one of the air outlet apertures when the flap is in the first position.

13. A valve according to claim 7, wherein said first portion includes a plurality of spaced apart closing leafs.

* * * * *